United States Patent [19]

Schocket

[11] Patent Number: 4,826,478
[45] Date of Patent: May 2, 1989

[54] ANTERIOR CHAMBER TUBE SHUNT TO AN ENCIRCLING BAND, AND RELATED SURGICAL PROCEDURE

[76] Inventor: Stanley Schocket, 3509 Anton Farms Rd., Baltimore, Md. 21208

[21] Appl. No.: 87,802

[22] Filed: Aug. 21, 1987

Related U.S. Application Data

[63] Continuation-in-part of Ser. No. 877,342, Jun. 23, 1986, Pat. No. 4,722,724.

[51] Int. Cl.$^4$ .............................................. A61M 27/00
[52] U.S. Cl. ........................................ 604/8; 604/294
[58] Field of Search ...................................... 604/8–10, 604/294, 266

[56] References Cited

U.S. PATENT DOCUMENTS

| | | | |
|---|---|---|---|
| 3,736,939 | 6/1973 | Taylor | 604/265 |
| 3,788,327 | 1/1974 | Donowitz et al. | 128/350 R |
| 3,976,081 | 8/1976 | Lapidot | 604/265 |
| 4,249,535 | 2/1981 | Nargest | 604/265 X |
| 4,402,681 | 9/1983 | Haas et al. | 604/9 |
| 4,457,757 | 7/1984 | Molteno | 604/294 |
| 4,554,918 | 11/1985 | White | 604/10 |
| 4,604,087 | 8/1986 | Joseph | 604/9 |

OTHER PUBLICATIONS

Hufnagel et al., Surgery, Vol. 61, No. 1, pp. 11–16, 623-2, January 1967.
Schocket et al., "Anterior Chamber Tube Shunt to an Encircling Band in the Treatment of Neovascular Glaucoma, Ophthalmology 89, pp. 1188–1194, 1982.
Schocket et al., "Anterior Chamber Tube Shunt to an Encircling Band in the Treatment of Neovascular Glaucoma and Other Refractory Glaucomas, Ophthalmology 92, pp. 553–562, 1985.
Krupin et al., "Valve Implants in Filtering Surgery," American Journal of Ophthalmology, Vol. 81, pp. 232–235, 1976.
Molteno et al., "Two-Stage Insertion of Glaucoma Drainage Implants," Trans. Opthal. Soc. N.Z., 31, pp. 17–26, 1979.
White, "A New Implantable Ocular Pressure Relief Device: A Preliminary Report," Glaucoma, 7, pp. 289–294, 1985.

Primary Examiner—Dalton L. Truluck
Attorney, Agent, or Firm—Fleit, Jacobson, Cohn & Price

[57] ABSTRACT

An implant and a surgical technique involving the anterior chamber tube shunt to an encircling band treatment for reducing neovascular and other refractory glaucomas is disclosed. The implant is a tube connected to a band. One end of the tube is located in the anterior chamber of the eye and the other end of the tube is mounted to the band, which is mounted around the equator of the eye. The length of the tube approximates the length of the band to initially restrict flow of aqueous from the anterior chamber and thereby prevent hypotony. Additionally, all surfaces of the implant may be treated with a heparin complex before implantation of the device.

7 Claims, 2 Drawing Sheets

ANTERIOR CHAMBER TUBE SHUNT TO AN ENCIRCLING BAND, AND RELATED SURGICAL PROCEDURE

This is a continuation in part application of U.S. Ser. No. 877,342, filed June 23, 1986, now U.S. Pat. No. 4,722,724 issued Feb. 2, 1988.

BACKGROUND OF THE INVENTION

1. Field of the Invention

The present invention relates to an implant and a surgical technique for treating neovascular glaucoma, and particularly to improvements in the anterior chamber tube shunt to an encircling band procedure.

2. Description of Prior Art

Glaucoma, a disease of the eye which may ultimately cause blindness, is caused by increased intraocular pressure. Since as early as 1906, surgical techniques have been attempted to treat glaucoma by lowering intraocular pressure. A modern surgical technique has been described by Schocket et al, in an article entitled "Anterior Chamber Tube Shunt to an Encircling Band in the Treatment of Neovascular Glaucoma", *Ophthalmology*, Vol. 89, No. 10, pp. 1188-1194, 1982, and in another article entitled "Anterior Chamber Tube Shunt to an Encircling Band in the Treatment of neovascular Glaucoma and other Refractory Glaucomas", Ophthalmology, Vol. 92, No. 4, pp. 553-562, 1985.

According to the teachings of the above mentioned articles, aqueous is shunted from the anterior chamber of the eye to the orbit in order to reduce the intraocular pressure. The aqueous escapes through a tube inserted into the anterior chamber which is connected to a band which encircles the circumference of the eye. The aqueous fluid is shunted to an encapsulated reservoir and then diffuses through the capsular wall into the orbit to thereby lower the intraocular pressure.

Approximately two weeks after such surgery, the implanted materials become surrounded by a fibrous capsule separating the implant from the host tissue, a capsule that is contiguous with the tissue but not adherent to the implant. The capsule is apparently an attempt to destroy or isolate what the host tissue recognizes to be a foreign body. This encapsulation is essential for success and recovery in response to the surgical procedure.

Although this above-described work was a significant advance over the art, the implant of this surgical procedure can be improved. First, the surgically treated eye could be subject to bleeding into the anterior chamber. This could potentially occur at the time of insertion of the tube into the anterior chamber or shortly thereafter. As a consequence, blood clotting could occur which could block the opening in the tube needed to transport the aqueous from the eye, cause an increase in intraocular pressure, and render the procedure ineffective. This especially could occur in patients with severe rubeosis iridis.

An additional problem that could result with the known implant is that the patient could suffer from hypotony for a time period lasting from implantation until formation of the fibrous capsule around the implanted materials. Hypotony occurs when aqueous outflow from the chamber exceeds aqueous production as seen after insertion of the implant and causes too low an intraocular pressure and a corresponding flat anterior chamber. This could lead to further pathologic problems such as cataracts, adhesions of iris to cornea or lens, and in eyes which have had prior surgery, hemorrhagic choroidal detachments with a resultant loss of vision.

Further, although encapsulation of the implant is necessary for success of the surgical procedure, limiting the thickness of the capsule wall is desirable since this allows less restrictive movement of aqueous fluid out of the encircling band into the orbit and thereby ensures a good flow of aqueous. The known procedure did not possess this desired benefit.

Others have sought to remedy these problems, most notably the hypotony problem which occurs shortly after surgical implantation.

U.S. Pat. No. 3,788,327 to Donowitz et al disclose a surgical implant device. The Donowitz et al device is designed to rest on the surface of the cornea whereby a shank-like member with a valve to control intraocular pressure is mounted through the eye into the anterior chamber. Because the device is physically mounted onto the eye itself, friction occurs between the eyelid and the device. Additionally, the escaping aqueous flows to the cornea and not to the orbit. Furthermore, the valve in the Donowitz et al device must be permanently mounted in the shank to control the pressure in the anterior chamber.

U.S. Pat. No. 4,402,681 to Haas et al disclose an artificial implant valve. This valve is disadvantageous in that it is mounted into the posterior segment of the eye, and therefore it is difficult to adjust or remove the valve in the event of surgical complications. Further, the valve must remain permanently mounted to the eye to be effective. In addition, the construction of the valve in the Haas et al patent is composed of several parts and is complex.

Krupin et al disclosed valve implants for reducing intraocular pressure in an article entitled "Valve Implants in Filtering Surgery", *American Journal of Opthalmology*, Vol. 81, No. 2, pp. 232-235, 1976. The Krupin et al implant consists of a supramid tube which is cemented to a silastic tube. The end of the supramid tube is beveled and surgically inserted into the anterior chamber. The silastic tube remains outside the anterior chamber and has on its surface horizontal and vertical slits which function as a unidirectional valve. The Krupin et al device poses problems in that the valve is located in the silastic tube outside the anterior chamber. Therefore, if there are problems with the device, the conjunctiva and Tenon's Capsule must be surgically re-entered. Further, the device is designed so that the valve must be permanently mounted in the device if the device is to be effective.

Molteno et al also have developed a method of treating glaucoma. See Molteno et al, "Two Stage Insertion of Glaucoma Drainage Implants", *Trans. Ophthal. Soc. N.Z.*, Vol. 31, pp. 17-26, 1979. According to the Molteno et al technique, a silicone tube is attached to a circular plate which is sutured to the globe. A silastic tube which is connected to the plate is sutured to the the sclera but is not inserted into the anterior chamber. Eight weeks later, a second operation is performed whereby the silastic tube is inserted into the anterior chamber. The Molteno et al procedure, therefore, requires two separate surgical operations to treat neovascular glaucoma and prevent hypotony.

White has disclosed a glaucoma pump shunt in "A New Implantable Ocular Pressure Relief Device: A Preliminary Report", Glaucoma, Vol. 7, pp. 289-294, 1985. The device consists of an inlet tube, an outlet tube, and a reservoir which connects the two tubes. Valves are located in both the inlet tube and the outlet tube, each valve located near the connecting reservoir. The end of the inlet tube located opposite from the connecting reservoir is mounted into the interior chamber. The reservoir is seated on the sclera and the posterior portion of the outlet tube is positioned in the sub-Tenon's space. This device is disadvantageous because of the intricate mounting of the reservoir and outlet tube, and because the inlet tube valve is located on the sclera and not in the anterior chamber, making it difficult to repair or replace the valve in case of failure. Additionally, because of the design of this system, the inlet and outlet valves are permanently mounted to the inlet and outlet tubes for the entire period when the device is implanted. Furthermore, the device is designed so that the reservoir permanently rests on the sclera and can potentially cause friction and erosion of the sclera and the conjunctive.

The inventor, in parent U.S. Application Ser. No. 877,342, filed June 23, 1986, prevents hypotony by utilizing a valve which takes the form of a temporary restriction. The valve is constructed so that it functions during the ten day to two week critical period when hypotony is most likely to occur. Thereafter, the valve is destroyed by a procedure such as a laser procedure, or the valve itself is made of a bio-destructible material such as collagen which automatically breaks down after the critical time period. Although this is an improvement upon existing technology, the presence of the restriction presents minor problems.

The problems associated with the restriction are twofold. First, due to the nature of the restriction, the silastic tube attached to a silicone band can become completely clogged because of its reduced cross-sectional area. Moreover, additional means are necessary to ultimately destroy the valve after hypotony is no longer a risk.

Thus, a need exists for a simplified surgical procedure to treat glaucoma which may be performed in one step where the implanted device is easily accessible is follow-up surgery is needed to correct complications. Further, a need exists to prevent hypotony shortly after the surgical device is implanted without requiring the use of flow restricting means. Additionally, a need exists to regulate the volume of aqueous flowing from the anterior chamber and to ensure that aqueous flows from the chamber to thereby prevent a buildup of intraocular pressure. Further, a need exists to prevent bleeding associated with the surgical technique and to prevent clogging of the implant caused by blood clots located in the opening or within the lumen of the tube of the implant.

SUMMARY OF THE INVENTION

A purpose of the present invention is to provide a one-step surgical procedure whereby an implant is constructed by suturing one end of a silastic tube to a silicone band whereby the outer end of the silastic tube is mounted to be displaced away from the silicone band. The silicone band is positioned around the globe beneath the four rectus muscles of the eye. The displaced end of the silastic tube is then inserted via a needle tract into the anterior chamber under a scleral flap hinged at the limbus, defined by cauterizing the incision tract with a needle, inserting the needle into the anterior chamber and withdrawing it, injecting hyaluronic acid into the anterior chamber, and inserting the end of the silastic tube into the anterior chamber through a head of hyaluronic acid. The remainder of the silastic tube which is not mounted into the anterior chamber is mounted inside a groove of the silicone band with the grooved side facing the sclera when positioned around the eye. The silastic tube is sized lengthwise so that its length corresponds almost exactly to the length of the silicone band. By utilizing this length for the silastic tube, hypotony is controlled without requiring the use of a valve or flow restriction.

When the silicone band is sutured to the sclera of the eye, the orbit forms an encircling capsule around the implant where it has been mounted. Although this is necessary for the effective diffusion of aqueous into the orbit, it would be desirable to limit the density of the capsule wall since this would allow less restrictive movement of aqueous fluid out of the encircling reservoir and into the orbit. Therefore, all surfaces of the silastic tube and silicone band are coated with a heparin complex prior to surgical insertion to obtain a much less dense fibrous capsule. In addition to limiting the density of the capsule wall, the heparin serves to prevent the formation of clots along the aqueous pathway in contact with the implant.

Accordingly, it is an object of the present invention to provide an implant and a surgical technique to treat neovascular and other refractory glaucomas by reducing intraocular pressure in the anterior chamber without causing the patient to be subjected to dangerous side effects.

A further object of the present invention is to provide an implant and a surgical technique for treating neovascular and other refractory glaucomas whereby a sufficient pressure is maintained in the anterior chamber at the time of surgery and shortly thereafter to prevent hypotony.

A further object of the present invention is to provide an implant and a surgical procedure for treating neovascular and other refractory glaucomas whereby bleeding and blood clotting are minimized during and shortly after surgery.

An additional object of the present invention is to provide an implant and a surgical technique for treating aqueous from the anterior chamber to the orbit is maintained and whereby the body forms a thin walled fibrous capsule around the surgical implant.

Other objects and features of the present invention will become apparent to those skilled in the art when reference is made in the following description taken in conjunction with the accompanying drawings.

DETAILED DESCRIPTION OF THE DRAWINGS

Figure 1:
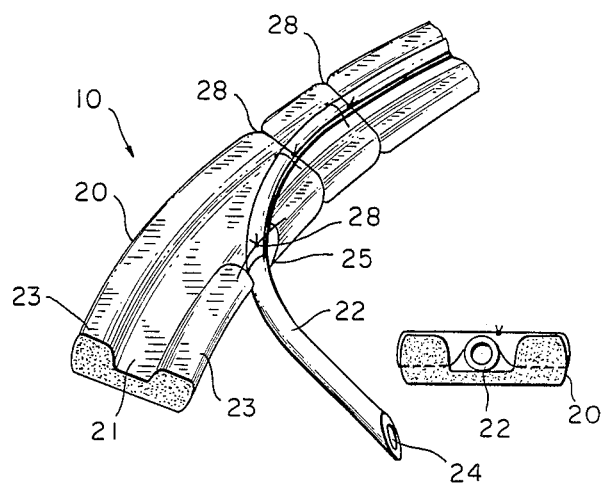
FIG. 1 is a view of a surgical implant which embodies the teachings of the instant invention.

In describing the invention illustrated in the drawings, specific terminology will be resorted to for the sake of clarity. However, the invention is not intended tobe limited to the specific terms so selected, and it is to be understood that each specific term includes all technical equivalents which operate in a similar manner to accomplish a similar purpose.

Referring now to the drawings, and more particularly to FIG. 1, the basic elements of the inventive surgical implant are collectively designated as 10. Generally, implant 10 is constructed by mounting a silastic tube 22 to a silicone band 20. In the preferred embodiment of the present invention, silicone band 20 is a No. 20 type silicone band approximately 76 millimeters long and silastic tube 22 is 70 millimeters long, with an inside diameter of 0.30 millimeters and an outside diameter of 0.64 millimeters. In the preferred embodiment of the present invention, band 20 and tube 22 are both made of silicone polymers.

Silicone band 20 has a U-shaped groove 21 located at the center of one side and extending throughout the length of band 20. One end of tube 22 is placed in groove 21 and is fastened to band 20 by Supramyd sutures 28 or by any suitable equivalent.

The U-shaped groove 21 in silicone band 20 is defined by raised parallel sides 23 joined together by a groove bottom member. If the end of tube 22 which is mounted in groove 21 of band 20 becomes misaligned with groove 21 and intersects either side 23 allowing the tube end to touch with the episclera instead, fibrous tissue could encapsulate the intersection of tube 22 with side 23, block the opening of tube 22, and decrease the effectiveness of the implant. Therefore, it is important that tube 22 be securely mounted in the center of groove 21 to prevent encapsulation and clogging of tube 22.

To further secure the tube terminus, ¾ of the inner wall of tube 22 is removed and the remaining tongue of silastic tube 22 is permanently secured to band 20 by a 5-0 Supramyd suture. The silicone band 20 inhibits fibrous ingrowth into silastic tube 22 only if tube remains in contact with band 20.

On one of raised sides 23 an indentation 25 is constructed by removing part of side 23. The end of tube 22 not secured in groove 21 is inserted in indentation 25 and is fastened to side 23 in indentation 25 by suture 28 or any other suitable fastening means.

The end of tube 22 which is mounted in indentation 25 of side 23 is obliquely cut to maximize the opening 24 of tube 22, which opening is designed to reside in the anterior chamber.

Insertion and operation of implant 10 is as follows. A 360° peritomy is made posterior and parallel to the limbus at the junction of cornea and sclera, except superiorly where the conjunctival incision is extended posteriorly. In the preferred embodiment of the surgical technique, the peritomy is made 4 to 5 millimeters posterior to the limbus and the conjunctival incision is extended posteriorly for 8 millimeters. A vitreous tap is performed if, despite pharmaceutical treatment, the intraocular pressure is equal to or greater than 40 millimeters of mercury. Traction sutures are then placed under the four rectus muscles.

Figure 2:
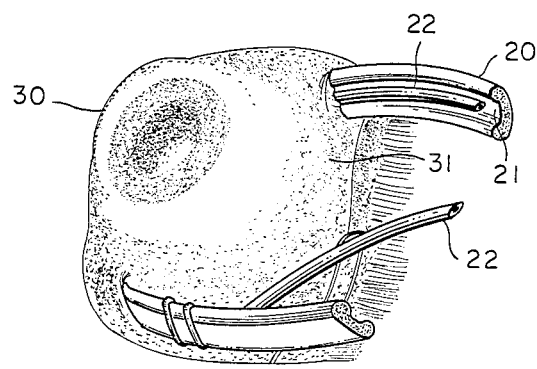
FIG. 2 is a view of the surgical implant where the silicone band is positioned around the globe and where the silastic tube is located anteriorally just temporal to the superior rectus muscle.
Figure 4:
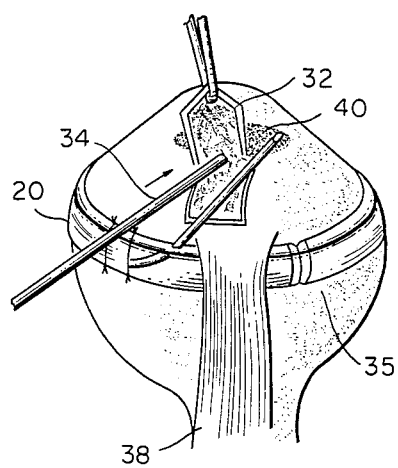
FIG. 4 is a view of an eye being treated with a cauterized needle before insertion of the silastic tube into the anterior chamber.
Figure 5:
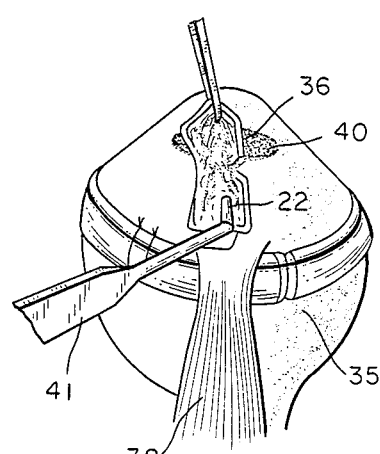
FIG. 5 is a view of the silastic tube being inserted into the anterior chamber.

Referring to FIGS. 2, 4, and 5, band 20 as illustrated is positioned so as to extend completely around the maximum circumference of the eye 30 (i.e., the equator), beneath the four rectus muscles 38, with groove 21 facing sclera 31. Band 20 is fastened to sclera 31 by fasteners such as sutures 35 (See FIGS. 4, 5) in the four quandrants such that the anterior edge of band 20 is located just posterior to the insertion of the rectus muscles. In the preferred surgical technique, the anterior edge is located approximately 10 to 12 millimeters from the limbus. The end of silastic tube 22 which is extended from band 20 should emerge from band 20 anteriorly, just temporal to the superior rectus. (See FIGS. 2, 4).

As FIGS. 2, 4 and 5 clearly show, tube 22 extends in groove 21 around the equator of the eye over nearly the entire length of the groove.

Figure 3:
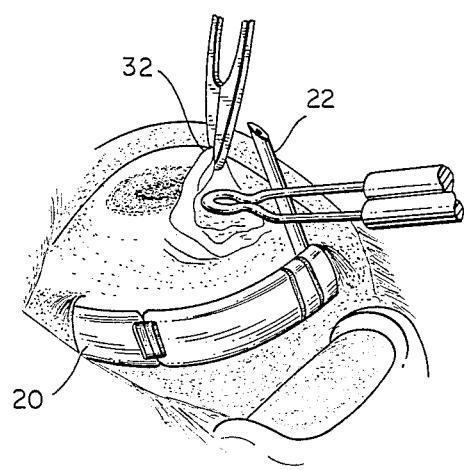
FIG. 3 is a view of an eye before the surgical implant is inserted into the anterior chamber.

Referring to FIG. 3, a limbal based scleral flap 32 is raised and carried forward into the clear cornea. According to the preferred surgical technique, the flap measures 4 millimeters by 4 millimeters and is carried forward one millimeter into the clear cornea. Tube 22 is then anchored to the posterior and temporal edges of the scleral bed so that, on insertion, tube 22 lies over the nasal iris. In the preferred surgical technique utilized when practicing the invention, anchoring is accomplished by 10-0 nylon sutures.

Entry to anterior chamber 40 is effected first by directing a needle 34 into anterior chamber 40 (See FIG. 4). In the preferred surgical technique, the needle is 25-gauge (0.5 mm outside diameter) and is bent to allow entry parallel to the iris. To prevent bleeding caused by entry of the needle 34 into a highly neovascularized angle, needle 34 is touched with a wet-field cautery to obtain coagulation of the ruptured bleeding angle vessels upon insertion. On withdrawal of needle 34, anterior chamber 40 becomes shallow due to loss of aqueous. Hyaluronic acid (Healon ®) is injected into anterior chamber 40 through a 23-gauge needle (0.65 mm outside diameter) to restore anterior chamber 40 with hyaluronic acid. In the preferred surgical technique, 0.1 to 0.3 milliliters of hyaluronic acid is injected to deepen the chamber to full depth. The needle is removed from the anterior chamber 40 and the hyaluronic acid refluxes to form a bead 36 which indicates the opening to the anterior chamber 40 (see FIG. 5).

Figure 6:
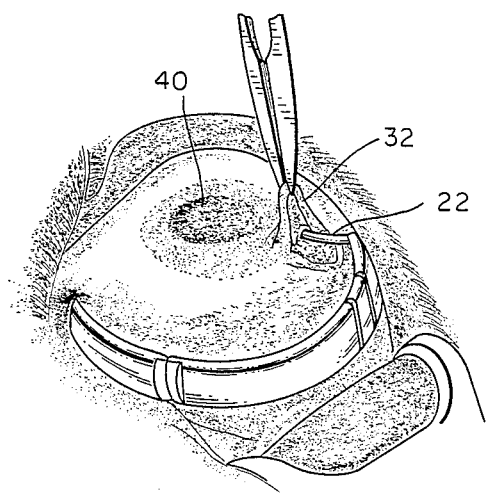
FIG. 6 is a view of an eye after the silastic tube is inserted into the anterior chamber.

The end of tube 22 lying over the nasal iris is compressed between the jaws of a microforceps 41 (see FIG. 5), and is introduced into anterior chamber 40 by insertion through bead 36. Tube 22 is inserted into anterior chamber 40 until the desired length of tube 22 has entered the chamber (See FIG. 6). According to the preferred surgical technique utilized when practicing the present invention, the tube should extend approximately 3 millimeters into the anterior chamber.

Figure 7:
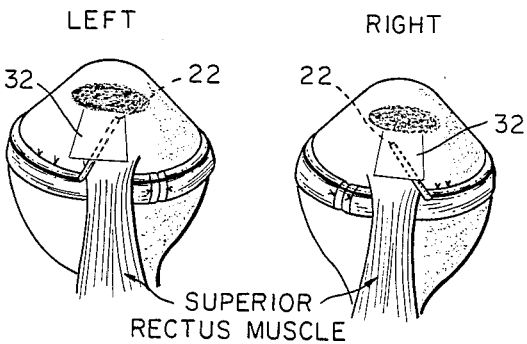
FIG. 7 is a view of the left eye and the right eye after completion of the inventive surgical procedure.

Scleral flap 32 is then closed by suitable means such as nylon sutures located at the two posterior corners. (See FIG. 7). Scleral flap 32 is made slightly temporal to the mid-line in each eye to allow coverage of silastic tube 22, which is angled towards the nasal iris. Tenon's capsule over the tube is closed separately from the conjunctiva by suitable means such as a running 7-Vicryl suture. The conjunctiva is then closed by a suitable means such as a continuous 6-0 plain cat gut suture. 40 mg of Gentamicin sulfate and 4 mg of dexamethasone phosphate are injected into the inferior subconjunctival space to complete the surgical technique.

This procedure results in the formation of a fibrous capsule surrounding silicone band 20. The capsule forms within ten days to two weeks after implantation and is apparently an attempt of the body to destroy or isolate what the host tissue recognizes to be a foreign substance, namely, silicone band 20. Aqueous fluid draining from anterior chamber 40 through tube 22 into band 20 is known to diffuse into and expand this capsule. Fibrous encapsulation of silicone band 20 is essential for the success of the surgical procedure because the capsule acts as the wall of the reservoir through which aqueous diffuses into the orbit to be picked up by orbital vessels which return the fluid to the general blood circulation.

To prevent hypotony from occurring during the formation of the fibrous capsule, tube 22 is sized to that its length approximates the length of band 20. For a typical human eye, the circumference of the eye is approximately 74 mm. Thus, the length of band 20 is approximately 76 mm.

The production of aqeous by the eye is approximately 2.54 microliters of aqueous per minute. In the past, such as the implant disclosed in U.S. Ser. No. 877,342, the length of tube 22 was approximately 30 mm. By utilizing this length, the rate of diffusion of aqueousf romthe anterior chamber to the silicone band was approximately 5.86 microliters per minute at a pressure of 18 mm of Hg. This flow rate would cause hypotony as the anterior chamber would tend to flatten. Thus, as discussed above, a restriction was necessary to limit the flow rate.

In the present invention, it was discovered that if the length of tube 22 would approximate the length of band 20, the flow rate of aqueous from the anterior chamber would be reduced to 3.54 microliters per minute at 18 mm of Hg. This flow rate is signficiantly low enough to prevent hypotony as the anterior chamber would not flatten due to the loss of aqueous. Moreover, this flow rate is established without requiring the use of a flow restriction. Rather, it is the length of tube 22 which causes this remarkable decrease in flow of aqueous.

To limit the density of the fibrous capsule walls (i.e., to maximize fluid flow and prevent clotting), a more bioreactive silicone implant may be inserted. One such method of creating a more bioreactive silicone implant is to fix a heparin complex to the silicone polymer.

Heparin, a substance normally found in ocular tissues, is an acid mucopolysaccharide or glycosaminoglycan, and is therefore a mroe bioreactive material than a silicone polymer. The heparin fixing process consists of immersing implant 10 in a solution of heparin-quaternary ammonium compound-complex in an organic solvent, removing the organic solvent, and sterilizing by gas or heat. The amount of complex fixed to all surfaces of implant 10 is approximately 40 mg/cm$^2$; the surface concentration is controlled by the concentration of the complex and the duration of the immersion.

The complex between heparin and tridodecylmethylammonium chloride (TDMAC) is formed when heparin, an acid mucopolysaccharide with an overall negative charge, is exposed to the TDMAC ammonium ion which is positively charged.

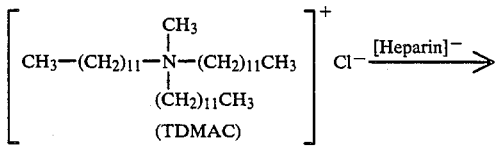

Heparin-TDMAC Complex

To effectively coat tube 22 and band 20 with a heparin solution, all surfaces of tube 22 and band 20 are treated with a one percent solution of the Heparin-TDMAC complex in 1:1 toluene/petroleum ether at room temperature for 30–60 seconds. Tube 22 and band 20 are then flushed with compressed air, and dried overnight in a vacuum oven to remove traces of the volatile organic solvent.

During the immersion process, the surface of the silicone polymer is swollen by the organic solvent, allowing penetration of the polymer surface by the hydrophobic hydrocarbon chains of the TDMAC portion of the complex. Removal of the organic solvent by evaporation results in firm fixation of the complex to the polymer surface as the polymer shrinks back to normal size. The surface-bound complex on polymers such as the present silicone implant is resistant to elution by saline or blood. Surface-bound heparin apparently causes thromboresistance in the same way as heparin does in solution. The presence of a heparin complex on the surface of silicone polymers probably simulates the naturally occurring heparin coat of the endothelium, thereby decreasing protein, leukocyte and platelet adherence, and resulting in prolonged coagulation time.

The heparin coating to all surfaces of tube 22 and band 20 effectively reduces the thickness of the fibrous capsule because the coating prevents the host tissue from fully recognizing the implant as a foreign body, and thus allows aqueous to flow through tube 22 into band 20 and diffuse through band 20 to the encapsulating fibrous tissue more rapidly.

Further, the heparin coating of silastic tube 22, acts to prevent tube obstruction by blood clots. A low intraocular pressure of 10 mm Hg is capable of flushing blood from heparinized tube 22 in 1 to 2 seconds whereas in a non-heparinized tube the intraocular pressure must be 60 mm Hg to flush the tube. If blood remains in the non-heparinized tube for 30 minutes, a pressure of 60 mm Hg is incapable of flushing the tube whereas in heparinized tube 22 the clot is expelled after 2 seconds.

From the above, it should be apparent that many modifications and variations of the present invention are possible. It is therefore to be understood that, within the scope of the appended claims, the invention may be practiced otherwise than as specifically described.

What is claimed is:

1. An implant for use in a surgical technique to treat neovascular or refractory glaucomas, said implant comprising:

a tube sized so that a first end thereof maybe inserted into the anterior chamber of the eye, a band sized so as to extend completely around the equator of the eye, said band having a U-shaped groove formed therein which extends throughout the length of said band, said band sized to surround said tube, a second end of said tube being mounted in said groove, said tube extending in said groove around the equator of the eye over nearly the entire length of said groove, and the first end of said tube having an oblique opening.

2. The implant according to claim 1, wherein said tube and said band are both made of silicone polymers.

3. The implant according to claim 1, wherein said implant has a heparin complex fixed to all surfaces of said tube and to all surfaces of said band.

4. The implant according to claim 1, wherein said tube is approximately 70 mm in length.

5. The implant according to claim 1, wherein the length of said tube is approximately 90 percent of the length of said band.

6. A method for treating neovascular or refractory glaucomas with a surgical implant, said method comprising the steps of:

providing a band sized to fit around the equator of an eye, the band including a U-shaped groove extending throughout the length of said band;

providing a tube sized to fit in said U-shaped groove around the equator of the eye over approximately the entire length of the U-shaped groove;

placing said tube in said U-shaped groove;

securing one end of the tube into the anterior chamber of the eye;

mounting the band around the equator of the eye;

inserting the other end of said tube into the anterior chamber of the eye;

restricting the flow of aqueous from the anterior chamber because of the length of the tube;

said aqueous flowing through said tube, into said band, and then diffusing from said band into the orbit.

7. A method according to claim 6, which includes the step of treating all surfaces of said tube and said band with a heparin solution prior to mounting said band around the equator of the eye.

* * * * *